United States Patent [19]
Katzman

[11] Patent Number: 5,962,335
[45] Date of Patent: *Oct. 5, 1999

[54] BREATH TEST FOR DETECTION OF DRUG METABOLISM

[75] Inventor: Daniel E. Katzman, Jerusalem, Israel

[73] Assignee: Oridion Medical Ltd., Jerusalem, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/778,589

[22] Filed: Jan. 3, 1997

[51] Int. Cl.$^6$ ....................................................... G01N 1/22
[52] U.S. Cl. ............................ 436/181; 436/56; 436/133; 436/173; 436/900; 422/83; 422/84; 73/23.3
[58] Field of Search ............................ 436/56, 106, 113, 436/127, 133, 173, 175, 181, 900, 901; 422/61, 83, 84; 73/23.3

[56] References Cited

U.S. PATENT DOCUMENTS

| | | |
|---|---|---|
| 3,649,199 | 3/1972 | Littlejohn ................................ 436/178 |
| 4,298,347 | 11/1981 | Walsh ....................................... 436/133 |
| 4,676,974 | 6/1987 | Hofmann et al. ..................... 436/900 X |
| 4,830,010 | 5/1989 | Marshall ................................. 600/300 |
| 5,063,275 | 11/1991 | Rosenfeld et al. ...................... 250/343 |
| 5,100,779 | 3/1992 | Watkins ..................................... 435/25 |
| 5,317,156 | 5/1994 | Cooper et al. .......................... 250/345 |
| 5,386,832 | 2/1995 | Wagner et al. .......................... 600/532 |

*Primary Examiner*—Maureen M. Wallenhorst
*Attorney, Agent, or Firm*—Fish & Neave; Jeffrey H. Ingerman; Joel Weiss

[57] ABSTRACT

A breath test for determining the rate of metabolism of a drug is described. First, a safe and effective amount of the drug, preferably appropriately labelled and most preferably isotopically-labelled, is administered to a subject. After a suitable time period, the exhaled breath of the subject is analyzed to determine the concentration of a metabolite. The concentration of the metabolite is then used to determine the rate of metabolism of the drug. A breath test kit is also described. Such a breath test kit would include an item or items necessary for performing at least one of the methods of determining the rate of metabolism of a drug in a subject. For example, such a breath test kit could include an isotopically-labelled drug to be administered to the subject.

4 Claims, No Drawings

BREATH TEST FOR DETECTION OF DRUG METABOLISM

FIELD AND BACKGROUND OF THE INVENTION

The present invention relates to a breath test for the detection of a drug metabolite and, more particularly, to a breath test which can be used to analyze the rate of metabolism of a drug.

Drugs can be broadly defined to include any chemical agent which affects living processes. Generally, however, the term "drug" is used to refer to any chemical agent with therapeutic effects. By "therapeutic effects", it is meant that the chemical agent is useful in the prevention, diagnosis and/or treatment of disease. Hereinafter, unless otherwise stated, the term "drug" will be taken to be any chemical agent with therapeutic effects.

Increasing knowledge about human physiology and disease has brought an exponentially increasing number of new drugs onto the market. These new drugs provide more effective treatments for many diseases, such as cancer, AIDS and bacterial infections which are resistant to formerly effective medications. However, these new drugs themselves can cause mild to severe side effects and even idiopathic disease, which is a disease state caused by the drug itself. These undesirable and even dangerous reactions are directly related to the concentration of the drug in the body.

The concentration of the drug in the body, in turn, is regulated both by the amount of drug ingested by the subject over a given time period, or the dosing regimen, and the rate at which the drug is eliminated from the body. Hereinafter, the term "subject" refers to a human or lower animal to whom the drug is administered. The drug can be eliminated in two different ways, depending upon the molecular structure of the individual drug. First, the drug can be chemically modified into an inactive component or components which are then excreted. Second, the drug can be excreted from the body in a substantially unaltered form. Hereinafter, the term "elimination" of the drug is defined as the excretion or the chemical modification of the drug.

Chemical modification of the drug is a common pathway for elimination of the drug. Such modification most frequently occurs in the liver, although it can also take place in the blood, the kidney and other tissues. Modification can be classified as either synthetic or nonsynthetic [L. S. Goodman and A. Gilman, eds, *The Pharmaceutical Basis of Therapeutics*. The Macmillan Company, 1970, p.11]. Nonsynthetic modification involves such chemical reactions as oxidation or hydrolysis, often resulting in the cleavage of the drug molecule into two or more inactive molecules. Synthetic modification results in the formation of a chemical bond between the drug and an endogenous substrate such as a carbohydrate or amino acid. In either case, the modified drug can be referred to as a "metabolite" and the process of modification as "metabolism".

Identifying the type of metabolism which a particular drug will undergo in the body is further complicated by a number of factors. First, many drugs will be subject to a number of metabolic pathways within the body; that is, they will be able to undergo several different types of chemical modification. Second, although the choice of pathway or pathways is at least partly dependent upon the structure of the drug, predicting which pathway or pathways will be used is very difficult, and must usually be done through experimentation. Third, the particular metabolic pathway used will also depend upon the physiology of the individual subject. For example, a subject with hepatic dysfunction may eliminate a drug very differently from a subject with normal liver function. Fourth, the presence of other chemicals within the body can also change the metabolic pathway used by a particular drug. This can result in particularly dangerous side effects in those subjects taking multiple drugs simultaneously, or even in subjects ingesting non-therapeutic substances such as nicotine, since one drug can in effect overwhelm the capacity of a particular pathway, preventing other drugs from being properly modified. Of course, all of these factors also affect the rate at which at a particular drug is eliminated or "cleared" from the body. Thus, the particular type of chemical modification, and the rate at which this modification occurs, depends upon both the structure of the drug itself, and upon factors within the individual subject to whom the drug is administered.

When a new drug is undergoing clinical trials, both the rate at which the drug is eliminated from the subject and the type of metabolite(s) formed are determined. The rate of elimination will of course vary from subject to subject, so the drug must be tested in many individuals to produce an average elimination rate. Preferably, of course, many different groups of individuals will be tested, since children eliminate drugs more slowly than adults, for example, even when the dosage is given by body weight. The type of metabolite(s) formed must also be determined to indicate which pathway or pathways will be used. For example, if the drug is largely eliminated by the liver, a lower dosing regimen may be required for subjects with hepatic dysfunction. Thus, dosing regimens, or the rate and amount of drug which should be administered to a subject, can be determined from this information.

These dosing regimens have one major drawback, however: they are not tailored to the individual. At best, different regimens may be proposed for large groups of individuals, but even that is not always done. Thus, the geriatric patient with hepatic dysfunction, who is taking multiple drugs and who may have a low body weight, could potentially be given the same amount of a drug at the same rate as a young adult. Such a situation can be particularly dangerous for hospitalized patients, who frequently have both major organ dysfunctions and require multiple drug therapy.

"Therapeutic drug monitoring" is already used in order to adjust dosing regiments for individual patients in certain cases. In therapeutic drug monitoring, the concentration of a drug is measured in the blood of a patient, generally either just after the administration of a dose or just before the administration of the next dose [A. Goodman Gilman et al., eds, *Goodman and Gilman's The Pharmacological Basis of Therapeutics*, Pergamon Press, 1991, p. 30-31]. Usually, the concentration of a drug is measured just before the administration of the next dose, in order to determine the rate at which the drug is being cleared from the body. The concentration of the drug is measured just after the administration of a dose if the drug is almost completely eliminated between doses. Of course, if the concentration of the drug is measured more than once, the rate of clearance from the body can be more accurately determined.

Examples of drugs for which therapeutic drug monitoring is used include cyclosporine, which is an immunosuppressive agent [A. Lindholm and J. Sawe, *Therapeutic Drug Monitoring*, 17:570–3, 1995]. Indeed, A. Lindholm and J. Sawe specifically state that successful immunosuppression depends upon the tailoring of individual dosing regimens.

In these cases, it would clearly be highly useful to have a test which is simple, rapid, reliable and non-invasive and which could allow medical professionals to easily tailor the dosing regimen for the particular patient.

Unfortunately, currently available tests are invasive, difficult to administer or require an extended period of time for analysis. For example, therapeutic drug monitoring currently requires the analysis of a blood sample. Such a test is both invasive and complex, requires a laboratory to perform the analysis and requires an extended time period for analysis. Furthermore, such a test cannot be done in the home of a patient and, if performed in a doctor's office, often requires even more time for the sample to be sent away to a laboratory. Finally, such a test is difficult to perform many times on the same patient, due to the invasive nature of the sampling mechanism, and to the delay between the time the sample is obtained and the time it is analyzed.

Another possible method to determine the proper dosing regimen for an individual is to analyze the rate of metabolism of the drug in that individual by measuring the concentration of a metabolite. Metabolites can be detected when excreted in urine, for example. The concentration of these metabolites in at least one, and preferably in repeated samples would allow the rate of metabolism to be measured. However, although urine is relatively easy to collect, a laboratory is still required for analysis. Furthermore, such an analysis may require an extended period of time. Finally, the increased accuracy obtained with repeated samples makes many of these tests impractical. Unless the patient is in a hospital, collecting repeated samples and bringing them to the doctor's office or clinic is time-consuming and unlikely to result in patient compliance.

U.S. Pat. No. 5,100,779 to Watkins (hereinafter referred to as "Watkins") discloses a breath test in which a radiolabelled "reference drug", erythromycin, which is known to be metabolized by cytochrome p-450 is administered to a subject and the concentration of radiolabelled carbon dioxide in the exhaled breath of the patient is then measured in order to determine cytochrome p-450 activity. This activity is then correlated to the rate of metabolism of other drugs by using additional factors such as the age of the subject. However, such a test is necessarily restricted to those drugs whose metabolism can be directly correlated to the measured cytochrome p-450 activity on erythromycin. Furthermore, if multiple drugs are being administered to one patient, or even if the patient is ingesting non-therapeutic substances such as nicotine, the metabolic behavior of any one drug can be strongly affected, as noted above. In that case, the metabolism of a drug relative to the "reference drug" could be difficult to predict. It would be much more useful to have a breath test which can directly measure the rate of metabolism of each drug individually, rather than relying upon the predictive value of results obtained with a reference drug.

There is thus a widely recognized need for, and it would be highly advantageous to have, a test for the rate of drug metabolism which is easy, reliable, rapid, substantially non-invasive and sensitive, and which could more easily be used for multiple measurements.

SUMMARY OF THE INVENTION

According to the present invention there is provided a method for measuring a characteristic of metabolism of a drug having a metabolite in a subject, including the steps of: (a) administering the drug to the subject; and (b) analyzing exhaled breath of the subject for a concentration of the metabolite after a suitable time period, the concentration indicating the characteristic of metabolism of the drug in the subject. Preferably, the exhaled breath of the subject is analyzed by a measuring instrument selected from the group consisting of an infrared spectrometer and a mass spectrometer. Also preferably, the drug is isotopically-labelled. Most preferably, the metabolite is either carbon dioxide, most preferably carbon-13 isotopically-labelled, or ammonia, most preferably nitrogen-15 isotopically-labelled. Alternatively and preferably, the metabolite is a substantially unchanged form of the drug and is either nitrogen-15 isotopically-labelled or carbon-13 isotopically-labelled.

The method also preferably includes the step of analyzing a reference sample of the exhaled breath of the subject, the reference sample being obtained substantially before the drug is administered to the subject.

According to another embodiment, there is provided a breath test kit for determining the characteristic of metabolism of a drug in a subject, comprising an appropriately labelled drug having a metabolite for administering to the subject, the metabolite being present in exhaled breath of the subject.

DESCRIPTION OF THE PREFERRED EMBODIMENTS

The present invention is of a breath test which can be used to determine the characteristic of metabolism of a drug in a subject. Specifically, the present invention can be used to determine this characteristic of metabolism by measuring the concentration of a metabolite in the exhaled breath of the subject after an appropriate amount of the drug has been administered to the subject. Hereinafter, the term "characteristic of metabolism" includes whether such metabolism occurs, the rate of metabolism and the extent of metabolism. However, for clarity the aforementioned and following descriptions specifically describe the measurement of the rate of metabolism.

Breath tests as a non-invasive diagnostic tool are well known in the art. Generally, these tests involve the administration of a labelled substrate to the subject and the measurement of one or more cleavage products produced when the substrate is chemically cleaved. Such tests have been quite successfully used for the diagnosis of an infection by *Helicobacter pylori* and for the measurement of gastric emptying.

For example, U.S. Pat. No. 4,830,010 to Marshall describes a method of detecting *Helicobacter pylori* by orally administering isotopically-labelled urea to a subject. *Helicobacter pylori* produces a large quantity of the enzyme urease, which hydrolyzes urea to form carbon dioxide and ammonia. Either one or both of these hydrolysis products can have the isotopic label. At least one isotopically-labelled product is then exhaled by the subject and can be detected in the exhaled breath of the subject by an appropriate measuring instrument. Thus, the breath test for diagnosing *Helicobacter pylori* relies upon the use of a substrate specifically intended for diagnostic purposes and not for therapeutic effect.

Other breath tests have been described to measure physiological processes such as the rate of gastric emptying. For example, gastric emptying rates were measured for solids and liquids by using [$^{13}C$]octanoate or [$^{13}C$]acetate, respectively, as the substrate [Duan, L.-P., Braden, B., Caspary, W. F. and B. Lembcke, *Digestive Diseases and Sciences*, 1995, 40:2200–2206]. The substrate was administered to the subject and the exhaled breath of the subject was measured with a mass spectrometer. Similarly to the breath test for diagnosing *Helicobacter pylori*, both substrates were specifically intended as diagnostic, rather than therapeutic, agents.

As noted above, the present invention is of a breath test which can be used to determine the rate of metabolism of a drug in a subject. Thus, the breath test of the present invention is clearly different from these prior art tests, since the prior art tests use the isotopically-labelled substrate to measure the rate of a general physiological process, such as gastric emptying, while the breath test of the present invention uses an isotopically-label led drug to measure the rate of metabolism of that drug. Furthermore, the breath test of the present invention is intended to be used with drugs of therapeutic value outside the breath test; while the substrates of prior art tests are not intended to have therapeutic value apart from their use in the tests themselves. Finally, the measurement of a physiological process is incidental to the breath test of the present invention, since as noted above, metabolism of a drug can incorporate many different physiological processes, all of which contribute to the measured rate of metabolism. Thus, the breath test of the present invention will not necessarily measure the rate of any one physiological process, and it is not necessary to identify a particular physiological process in order for the measurement of the rate of drug metabolism to be successful.

The breath test of the present invention can be performed as follows. First, the drug is administered to the subject. Next, the exhaled breath of the subject is analyzed after a suitable time period for a concentration of a metabolite of the drug, the concentration indicating the rate of metabolism of the drug in the subject. To aid detection of the metabolite, the drug is preferably appropriately labelled, and most preferably isotopically-labelled. Hereinafter, the term "appropriately labelled" is defined as having a label which enables a metabolite of the drug to be detected in the exhaled breath of the subject. Such a breath test has a number of advantages over conventional methods for determining the concentration of a drug in the subject. Not only is a breath test non-invasive, it is also more rapid than analyzing blood samples and it can also be performed multiple times on the subject.

The following examples more fully illustrate how such a test can be performed. For the purposes of clarity, these examples will discuss isotopically-labelled drugs, it being understood that any appropriately labelled, or even non-labelled, drug can be used in the breath test.

EXAMPLE 1

Methods for Performing a Breath Test to Determine the Rate of Metabolism of a Drug The general method for determining the rate of metabolism of a drug by using a breath test can be described as follows (examples for specific drugs are given below). Preferably, the exhaled breath of the subject is analyzed before the drug is administered to the subject. This "reference sample" gives a baseline for the concentration of the metabolite in the breath of the subject. Next, a safe and effective amount of the drug, preferably appropriately labelled, is then administered to the subject. After a suitable time period, the exhaled breath of the subject is analyzed to determine the concentration of a metabolite. The concentration of the metabolite is then used to determine the rate of metabolism of the drug. This method can also be referred to as a "breath test".

The term "suitable time period" refers to the length of time required for a metabolite or metabolites to form and to be exhaled in the breath of the subject. Thus, the requisite time permits a number of events to occur. First, the drug must be absorbed by the subject. Next, the drug must be metabolized to form a metabolite or metabolites. Finally, the metabolite or metabolites must be exhaled in the breath of the subject.

The term "safe and effective amount of drug" refers to an amount of a drug which is sufficient to produce a detectable level of a metabolite or metabolites, without an untoward level of adverse side effects, such as toxicity, irritation, allergy or hypersensitivity responses. The level of any such side effects should be commensurate with acceptable risk/benefit ratios. The amount of drug administered does not need to have a therapeutic effect, however. For example, a small amount of an isotopically-labelled drug could be administered either alone, or in combination with non-labelled drug, as long as a detectable level of a metabolite or metabolites was produced. Alternatively and preferably, the labelled drug could be administered in sufficient quantities to have a therapeutic effect. Indeed, substantially all of the drug could preferably be labelled.

Examples of appropriate labels for the drug, and hence for the metabolite or metabolites, are those which can be detected by an appropriate measuring instrument, but which are substantially not harmful or toxic to the subject including, but not limited to, carbon-13 or carbon-14, oxygen-18 or nitrogen15, isotope-labelling. Such isotope-labelling should have substantially no effect on the therapeutic efficacy of the drug.

An isotope is a form of an element, such as carbon, with a specific mass. For example, carbon-12 has a mass of 12 atomic mass units. The term "isotope-labelling" means that the naturally more abundant isotope of each of these elements is at least partially replaced by a less abundant isotope. For example, the naturally more abundant carbon-12 atoms could be at least partially replaced by the less abundant carbon-13 atoms, permitting the metabolite or metabolites which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Therefore, preferably stable, non-radioactive isotopes such as carbon-13 are used as labels.

By the term "administered", it is meant that a method in accordance with good medical practice is used to introduce the drug into the subject. The drug can be administered to a subject in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection. Most preferably, administration is done orally, topically or by inhalation, as these methods are relatively non-invasive.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

If a small amount of a labelled drug is administered in combination with the non-labelled form of the drug, both forms of the drug should preferably be administered in a substantially similar manner. For example, if the non-labelled form of the drug is administered parenterally to the subject, the labelled form of the drug should also preferably be administered parenterally, for the most accurate measurement of the rate of metabolism, as described below. Most preferably, the labelled and non-labelled forms of the drug are administered simultaneously, so that the absorption, distribution and metabolism of the labelled drug is similar to that of the non-labelled drug.

Following the step of administering the drug to the subject, the exhaled breath of the subject is analyzed to detect a metabolite or metabolites. The metabolite or metabolites are detected by analyzing a gas sample of the exhaled breath of the subject with a measuring instrument. Such a gas sample can be obtained in a number of ways including, but not limited to, having the subject exhale or blow into a tube connected to the measuring instrument.

The type of measuring instrument used to detect the metabolite or metabolites depends upon the type of label. For example, if a carbon-13 isotopically-labelled drug is used, the carbon-13 isotopically-labelled metabolite or metabolites can be detected by using a measuring instrument including, but not limited to, a mass spectrometer or a gas analyzer, which is sensitive to the carbon-13 isotope. The ratio of the concentration of carbon-13 isotopically-labelled metabolite or metabolites to the concentration of carbon-12 metabolite or metabolites is then determined. Since carbon-12 is the more abundant isotope in nature, carbon-12 atoms are more abundant in unlabelled molecules. Thus, a higher carbon-13/carbon-12 ratio indicates a higher concentration of the carbon-13 isotopically-labelled metabolite or metabolites, which can be used to determine the rate of metabolism of the drug in the subject.

There are several important points which must be addressed in order for the breath test to be successful. First, if an isotopically-labelled drug is to be used, the reference sample is more important and should preferably be obtained, since small quantities of isotopically-labelled molecules always exist in nature. For example, a certain amount of carbon-13 carbon dioxide is present in the air normally. The reference sample can be used to establish a baseline of isotopically-labelled molecules in the exhaled breath of the subject. If multiple doses of the isotopically-labelled drug are to be administered, preferably a reference sample is obtained substantially before each dose is administered.

Second, the metabolite of the drug which is to be measured in the exhaled breath of the subject must be identified. However, since the metabolite or metabolites of any drug is established during experimentation and clinical trials, this requirement is fulfilled by substantially all drugs. One important point to note is that the metabolite present in the exhaled breath of the subject may be produced after more than one chemical modification of the drug and its metabolite(s). For example, carbon dioxide may be produced after a single chemical modification of one drug, but may only be produced after a plurality of chemical modifications of another drug. Again, the metabolism of a drug is determined during experimentation and clinical trials, so the number of modifications required is usually known for any given drug.

Third, the label which preferably is used to identify the metabolite in the exhaled breath of the subject should at least be present on a portion of the drug which forms the metabolite. For example, if labelled carbon dioxide is to be measured, the carbon atom on the drug which goes to the carbon dioxide metabolite should be labelled. Of course, other portions of the drug could also be labelled.

Another important point is that the preferably isotopically-labelled drug should preferably be administered by substantially the same method as the non-labelled drug. For example, if the non-labelled drug is given orally, the isotopically-labelled drug should also preferably be given orally. This ensures that the absorption rate, or the rate at which the drug enters the blood, is substantially similar for both the isotopically-labelled and non-labelled drugs, which is important for an accurate calculation of the rate of metabolism of the drug. This is particularly important when both the labelled and non-labelled drug are given simultaneously. Thus, the "suitable time period" depends, at least partly, on the form of administration of the drug.

A number of general methods for performing the breath test of the present invention is given below. Each method can be used with a different type of metabolite, as described below.

Method 1: Metabolite is Carbon Dioxide

This method can be used when at least one of the metabolites of the drug is carbon dioxide.

First, the exhaled breath of the subject is preferably analyzed to provide a "reference sample" as defined above. Next, an appropriate amount of a drug, preferably with an isotopically-labelled carbon atom, is administered to the subject. Preferably, such an isotopically-labelled carbon atom is carbon-13, although alternatively carbon-14 or oxygen-18, or some combination, can also be used. After a suitable period of time, the exhaled breath of the subject is analyzed for a concentration of isotopically-labelled carbon dioxide, which is a metabolite of the isotopically-labelled drug. The particular label on the carbon dioxide will of course depend upon the label on the drug itself.

Examples of measuring instruments which can be used with carbon-13 isotopically-labelled carbon dioxide include, but are not limited to, an infrared spectrometer. These infrared spectrometers are well known in the art, and have the advantage of being both rapid and accurate. Examples of such infrared spectrometers are disclosed in U.S. Pat. No. 5,063,275, herein incorporated by reference.

The concentration of the isotopically-labelled carbon dioxide can then be used to determine the rate of metabolism of the drug as follows. The rate of metabolism of the drug can be calculated from the initial dose of the isotopically-labelled drug, the amount of time elapsed between the time the initial dose is given and the time the exhaled breath of the patient is analyzed for a metabolite, and the concentration of the isotopically-labelled metabolite itself. Preferably, the concentration of isotopically-labelled carbon dioxide in the reference sample is used to calculate the true concentration of isotopically-labelled carbon dioxide metabolite.

Of course, unless the drug is given by a parenteral method, such as intravenous administration, which permits the drug to be instantly absorbed into the blood, the time required for the initial absorption of the drug must also be included in the calculation. Pharmacokinetic equations which permit the calculation of the rate of metabolism from the above data, as well as from empirical data on the behavior of the drug obtained during research and clinical trials, are well known in the art and could be used by someone ordinarily skilled in the art.

Furthermore, such information could then be used to determine the proper dosing regimen for the individual subject by someone ordinarily skilled in the art, again using pharmacokinetic equations. Indeed, *The Pocket Guide to Diagnostic Tests*, Chapter 4, states that when new methods of determining the plasma drug level are introduced, these new methods are used to determine the therapeutically effective concentrations of drug by comparison to the old methods, without additional clinical experimentation [*The Pocket Guide to Diagnostic tests*,http://dgim-www.ucsf.edu/ People/Publications/Detmer, as of Dec. 22, 1996]. Clearly, such comparison could also be performed for the breath test of the present invention.

Method 2: Metabolite is Ammonia

Method 2 is similar to Method 1, except that ammonia is the metabolite whose concentration is measured. In this case, a nitrogen atom of the drug molecule is preferably isotopically-labelled, preferably with nitrogen-15. As in the case of carbon dioxide in Method 1, although more than one nitrogen atom can be isotopically-labelled, at least the nitrogen atom which will go to the ammonia metabolite must be isotopically-labelled.

Of course, both carbon-13 isotopically-labelled carbon dioxide and nitrogen-15 isotopically-labelled ammonia could be present, providing that the drug has both labels. Both ammonia and carbon dioxide have the advantage of being molecules which are present in the exhaled breath of the subject.

Method 3: Metabolite is Drug Molecule

Certain drugs are eliminated, substantially unchanged, by excretion in the exhaled breath of the subject to whom they are administered. These drugs can be isotopically-labelled with carbon-13, carbon-14, oxygen-18 or nitrogen-15, or a combination of these labels. Since the drug molecule is excreted substantially unchanged in the exhaled breath of the subject, the drug molecule itself forms the metabolite. Hereinafter, the term "metabolite" can include the substantially unchanged drug molecule itself.

In general, such a breath test for the determination of the rate of metabolism of a drug has a number of advantages. First, analyzing the exhaled breath of a subject is inherently non-invasive, since the subject must simply blow or exhale air so that a measuring instrument can detect the presence of a metabolite or metabolites. Second, the exhaled breath of the subject can be analyzed in real time; that is, there is relatively little delay between the time the metabolite appears in the exhaled breath of the subject, and the time the concentration of such a metabolite is determined. Third, the rate of metabolism of the drug is determined directly from the concentration of a metabolite of the drug itself. This is particularly important when multiple drugs are administered simultaneously, since the metabolic behavior of any one drug can be strongly affected by the presence of other drugs, or even non-therapeutic substances such as nicotine, in the subject. In this case, the indirect measurement of the metabolic rate of a drug by using a "reference substrate", as in the Watkins prior art breath test, could be extremely misleading. Thus, such a breath test clearly has a number of advantages over previously known methods for determining the metabolic rate of a drug.

The breath test of the present invention could also be used for therapeutic drug monitoring. As described in the Background section above, therapeutic drug monitoring is the measurement of the concentration of drug in the blood of a subject in order to adjust the dosage regimen for that subject. One difficulty with current therapeutic drug monitoring is the necessity to withdraw numerous blood samples from the subject. The breath test of the present invention does not require blood samples, yet can be used to determine the concentration of a metabolite or metabolites in the exhaled breath of the subject, information which can then allow the proper adjustment of the dosing regimen for that subject.

EXAMPLE 2

Breath Test for Trimethadione

This Example describes the calculation of the rate of metabolism of trimethadione by using a breath test for an isotopically-labelled metabolite. Trimethadione is an antiepileptic drug, particularly effective for the treatment of petit mal epilepsy [A. Goodman Gilman et al., eds, *Goodman and Gilman's The Pharmacological Basis of Therapeutics*, Pergamon Press, 1991, p. 453 and L. S. Goodman and A. Gilman, eds, *The Pharmaceutical Basis of Therapeutics*, The Macmillan Company, 1970, p. 215–219]. Although no longer considered the first drug of choice for treatment of petit mal epilepsy, the long period of usage of trimethadione has enabled its behavior, including its metabolism, to be extensively studied. Thus, it is an ideal drug to use with the breath test of the present invention.

Trimethadione is generally administered orally. A number of body tissues, apart from the liver, can cleave trimethadione to form a number of metabolites, including carbon dioxide. Thus, trimethadione falls into the category of drugs described in Example 1, Method 1 above. A breath test for trimethadione could thus be performed as follows.

First, since trimethadione has carbon dioxide as a metabolite, at least the carbon atom which goes to carbon dioxide should preferably be isotopically-labelled, preferably with carbon-13. Preferably, the exhaled breath of the subject is first analyzed to serve as a reference sample, to determine a first concentration of carbon-13 isotopically-labelled carbon dioxide before the isotopically-labelled trimethadione is given. Next, the isotopically-labelled trimethadione is administered to the subject. As described above, the isotopically-labelled trimethadione is preferably administered orally, so that the route of administration of the labelled and non-labelled drugs is substantially the same. After a suitable time period, the exhaled breath of the subject is again analyzed and a second concentration of isotopically-labelled carbon dioxide is measured. At least the second concentration of isotopically-labelled carbon dioxide is then used to determine the rate of metabolism of trimethadione. Preferably, however, both the first and second concentrations of isotopically-labelled carbon dioxide are used in this calculation.

EXAMPLE 3

Breath Test for Nitrous Oxide

Nitrous oxide, or laughing gas, is the oldest gaseous inhalation anesthetic and is still used in certain circumstances today [A. Goodman Gilman et al., eds, *Goodman and Gilman's The Pharmacological Basis of Therapeutics*, Pergamon Press, 1991, p. 298–301]. Nitrous oxide is administered by inhalation to a subject and is mainly excreted unchanged in the exhaled breath of the subject.

Since nitrous oxide is an inhaled anesthetic, it represents a challenge for the use of a breath test in measuring the rate of metabolism. Since nitrous oxide is inhaled into the lungs of the subject, and a majority of nitrous oxide is excreted substantially unchanged by exhalation, accurately measuring the concentration of nitrous oxide as a metabolite is more difficult.

For example, if labelled nitrous oxide is given to the subject and the exhaled breath of the subject is then immediately analyzed, a significant quantity of the labelled drug in the exhaled breath of the subject could be nitrous oxide which was not absorbed by the subject.

Therefore, in order to accurately measure the metabolism rate of nitrous oxide, the "suitable period of time", which must elapse between administration and analysis of the exhaled breath of the subject, must allow for the lungs of the subject to be largely empty of the initial administered dose. One example of such a suitable period of time might be sufficient time for the subject to inhale air substantially absent of labelled nitrous oxide at least once before the exhaled breath is analyzed.

Apart from this difficulty, a breath test according to the present invention is an ideal method for measuring the rate of metabolism of inhaled anesthetics for a number of reasons. First, since the drug is largely excreted in the exhaled breath of the subject, sufficient quantities of the metabolite will be present in the exhaled gases for accurate measurements. Second, precise control of the concentration of inhaled anesthetics in the subject is particularly important because of their potentially dangerous side effects, such as respiratory depression and hypoxia. Third, these anesthetics are generally used for relatively short periods of time during surgery, so that accurate measurements of the concentration of the drug in the subject must be rapid and easy to make. Thus, a breath test according to the present invention could be very useful to help anesthetists accurately control the level of inhaled anesthetics in the subject.

Since nitrous oxide is the main metabolite, nitrous oxide falls into the category of Method 3 in Example 1 above. However, since nitrous oxide contains a nitrogen atom, it can also be used to demonstrate the detection of a metabolite labelled at the nitrogen atom, such as ammonia. A breath test for nitrous oxide could thus be performed as follows.

First, either the nitrogen atom or one of the oxygen atoms should preferably be isotopically-labelled. The nitrogen atom should preferably be labelled with nitrogen-15, or alternatively, one or both of the oxygen atoms should preferably be labelled with oxygen-18. Next, the isotopically-labelled nitrous oxide is administered to the subject. As described above, the isotopically-labelled nitrous oxide is preferably administered by inhalation, so that the route of administration of the labelled and non-labelled drugs is substantially the same. After a suitable time period, the exhaled breath of the subject is again analyzed and a concentration of isotopically-labelled nitrous oxide is measured. This concentration of isotopically-labelled nitrous oxide is then used to determine the rate of metabolism of nitrous oxide.

EXAMPLE 4

Breath Test for Paraldehyde

Paraldehyde is a sedative [A. Goodman Gilman et al., eds, *Goodman and Gilinan's The Pharmacological Basis of Therapeutics*, Pergamon Press, 1991, p. 367-368]. One problem with the use of paraldehyde is that it can cause severe side effects, such as respiratory depression, and even death at high doses. A breath test to determine the rate of metabolism of paraldehyde could prevent such poisoning.

Although paraldehyde is usually administered either orally or parenterally, the majority of the drug is excreted substantially unchanged in the exhaled breath of the subject. Paraldehyde therefore falls into the category of drugs described in Method 3, Example 1 above, in which the substantially unchanged drug itself is the metabolite. A breath test for paraldehyde could thus be performed as follows.

First, since substantially unchanged paraldehyde is the metabolite, any one of the nitrogen, carbon or oxygen atoms, or a combination thereof, could be isotopically-labelled. The preferred labels are nitrogen-15, oxygen-18, carbon-13 and carbon-14. The most preferred label is carbon-13. The use of a reference sample is less critical for paraldehyde since isotopically-labelled paraldehyde will only be exhaled after it has been administered to the subject, so a reference measurement is not as necessary.

Next, the isotopically-labelled paraldehyde is administered to the subject. As described above, the isotopically-labelled paraldehyde is preferably administered either orally or parenterally, so that the route of administration of the labelled and non-labelled drugs is substantially the same. After a suitable time period, the exhaled breath of the subject is analyzed and the concentration of isotopically-labelled paraldehyde is measured. The concentration of isotopically-labelled paraldehyde is then used t o determine the rate of metabolism of paraldehyde.

EXAMPLE 5

Breath Test for Cyclosporine

Cyclosporine is a cyclic peptide which is used for immunosuppression, to prevent the rejection of transplanted organs [A. Goodman Gilman et al., eds, *Goodman and Gilman's The Pharmacological Basis of Therapeutics*, Pergamon Press, 1991, p. 1267–1270]. It can be administered either orally or parenterally. One major drawback of cyclosporine is its toxicity, including severe renal toxicity. Thus, as noted in the Background section above, therapeutic drug monitoring is vital to ensure that an individual subject receives the minimum amount of cyclosporine necessary for successful immunosuppression. The breath test of the present invention could thus be very useful for the measurement of the rate of metabolism of cyclosporine in an individual subject.

As noted above, cyclosporine is a cyclic peptide composed of eleven amino acid residues. During metabolism of cyclosporine, a number of metabolites are formed as the bond s between these amino acid residues are broken. Ten of the eleven residues are the L-isomer, which is the normal isomeric form of amino acids. Furthermore, once certain of the bonds have been broken, certain of these residues will have α-amino groups. These amino acids can then be further metabolized through amino acid degradation pathways, such as the formation of ammonia from the removal of the α-amino group of an amino acid [*Biochemistry*, L. Stryer, ed., W. H. Freeman and Company, 1988, p. 495-496]. Thus, ammonia is at least one of the metabolites of cyclosporine. Cyclosporine therefore falls into the category of drugs which have ammonia as a metabolite, as described in Example 1, Method 2. A breath test for cyclosporine could therefore be performed as follows.

First, at least one of the nitrogen atom or atoms of cyclosporine which goes to ammonia should preferably be isotopically-labelled, preferably with nitrogen-15. Preferably, the exhaled breath of the subject is first analyzed to serve as a reference sample, to determine a first concentration of ammonia before the isotopically-labelled cyclosporine is given. Next, the isotopically-labelled cyclosporine is administered to the subject. As described above, the isotopically-labelled cyclosporine is preferably administered either orally or parenterally, so that the route of administration of the labelled and non-labelled drugs is substantially the same. After a suitable time period, the exhaled breath of the subject is again analyzed and a second concentration of isotopically-labelled ammonia is measured. At least the second concentration of isotopically-labelled ammonia is then used to determine the rate of metabolism of cyclosporine. Preferably, however, both the first and second concentrations of isotopically-labelled ammonia are used in this calculation.

Another potential metabolite of cyclosporine is carbon dioxide. This can be produced by the degradation of certain amino acids, such as tyrosine [*Biochemistry*, L. Stryer, ed., W. H. Freeman and Company, 1988, p.512]. Other amino acids enter the citric acid cycle via pyruvate, which can then be converted in a second reaction which yields carbon dioxide as one of the products [*Biochemistry*, L. Stryer, ed., W. H. Freeman and Company, 1988, p. 373]. In any case, carbon dioxide could be one of the metabolites of cyclosporine, in which case the breath test is performed as in Example 1, Method 1.

EXAMPLE 6

Breath Test Kit for Determining the Rate of Metabolism of a Drug

As described in Examples 1–5 above, the rate of metabolism of a drug can be determined in a subject by using a breath test. A breath test kit for determining the rate of metabolism of a drug in a subject would include an appropriately labelled drug having a metabolite for administering to the subject. The metabolite would need to be present in exhaled breath of the subject. For example, such a breath test kit could include an isotopically-labelled drug to be administered to the subject. Such isotopically-labelled drugs include, but are not limited to, those described in Examples 1–5 above.

As another example, the breath test kit could include, in addition to the isotopically-labelled drug, a device for administering the drug to the subject. For example, if the drug is to be inhaled, such a device could be an inhalation device of the type used to administer medications to patients with asthma. Alternatively, if the drug is to be administered orally, such a device could be a metered-dose syringe for oral administration, for example.

While the invention has been described with respect to a limited number of embodiments, it will be appreciated that many variations, modifications and other applications of the invention may be made.

What is claimed is:

1. A method for determining a therapeutic dosage regimen of a drug administered to a subject comprising the steps of:
   a. labeling a drug sought to be administered therapeutically to a subject with a non-radioactive isotope having a range of natural abundance and being detectable in a metabolite of said drug;
   b. prior to administration of said drug to a subject, measuring a first concentration of said non-radioactive isotope in the subject's breath;
   c. following said measuring step, administering said drug labeled with said non-radioactive isotope to the subject;
   d. following the administering step, measuring a second concentration of said non-radioactive isotope in the subject's breath, at least one of said first and second concentrations being within the range of natural abundance of the isotope; and
   e. employing the difference between said first and second concentrations to provide information as to a therapeutically acceptable dosage regimen of said drug based on metabolization of said drug by the subject.

2. A method according to claim 1 further comprising administering said drug to said subject in a therapeutically acceptable dosage regimen confirmed using said employing step e.

3. A method according to claim 1 wherein said measuring comprises the use of a measuring instrument selected from the group consisting of an infrared spectrometer and a mass spectrometer.

4. A method according to claim 1 wherein said non-radiactive isotope is carbon 13.

* * * * *